United States Patent
Murer

(10) Patent No.: US 9,566,422 B2
(45) Date of Patent: Feb. 14, 2017

(54) CREAM APPLICATION ASSEMBLY

(71) Applicant: Laura Murer, Kirkwood, MO (US)

(72) Inventor: Laura Murer, Kirkwood, MO (US)

( * ) Notice: Subject to any disclaimer, the term of this patent is extended or adjusted under 35 U.S.C. 154(b) by 0 days.

(21) Appl. No.: 14/692,916

(22) Filed: Apr. 22, 2015

(65) Prior Publication Data

US 2016/0310717 A1    Oct. 27, 2016

(51) Int. Cl.
*A61F 13/40*    (2006.01)

(52) U.S. Cl.
CPC .................................. *A61M 35/006* (2013.01)

(58) Field of Classification Search
CPC combination set(s) only.
See application file for complete search history.

(56) References Cited

U.S. PATENT DOCUMENTS

| | | | |
|---|---|---|---|
| 4,571,769 A | 2/1986 | Ford | |
| 5,076,424 A * | 12/1991 | Nakamura | A47K 10/3818 206/205 |
| 5,991,961 A | 11/1999 | Zurik | |
| D468,540 S | 1/2003 | Jessen | |
| 6,530,707 B1 | 3/2003 | Byrne et al. | |
| D497,451 S | 10/2004 | Hajianpour | |
| 6,835,019 B2 * | 12/2004 | White | A45D 34/042 401/174 |
| 7,309,180 B2 | 12/2007 | Russell et al. | |
| 7,559,108 B2 * | 7/2009 | Forte | A47L 25/005 15/104.002 |
| 8,158,689 B2 * | 4/2012 | Baker | A61L 15/425 428/159 |
| 8,646,142 B2 | 2/2014 | Ferrara et al. | |
| 8,662,774 B1 | 3/2014 | Wilson | |
| 2009/0093743 A1 | 4/2009 | Corzine | |

* cited by examiner

*Primary Examiner* — David Walczak

(57) ABSTRACT

A cream application assembly includes a handle that has a first end and a second end. The handle has a first portion slidably coupled to a second portion such that the handle has a telescopically adjustable length. An applicator is rotatably coupled to the handle and the applicator is infused with a cream. The applicator is used to apply the cream to a user.

1 Claim, 4 Drawing Sheets

CREAM APPLICATION ASSEMBLY

BACKGROUND OF THE DISCLOSURE

Field of the Disclosure

The disclosure relates to application devices and more particularly pertains to a new application device for providing peel away sheets infused with a cream to be applied to a user.

SUMMARY OF THE DISCLOSURE

An embodiment of the disclosure meets the needs presented above by generally comprising a handle that has a first end and a second end. The handle has a first portion slidably coupled to a second portion such that the handle has a telescopically adjustable length. An applicator is rotatably coupled to the handle and the applicator is infused with a cream. The applicator is used to apply the cream to a user.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
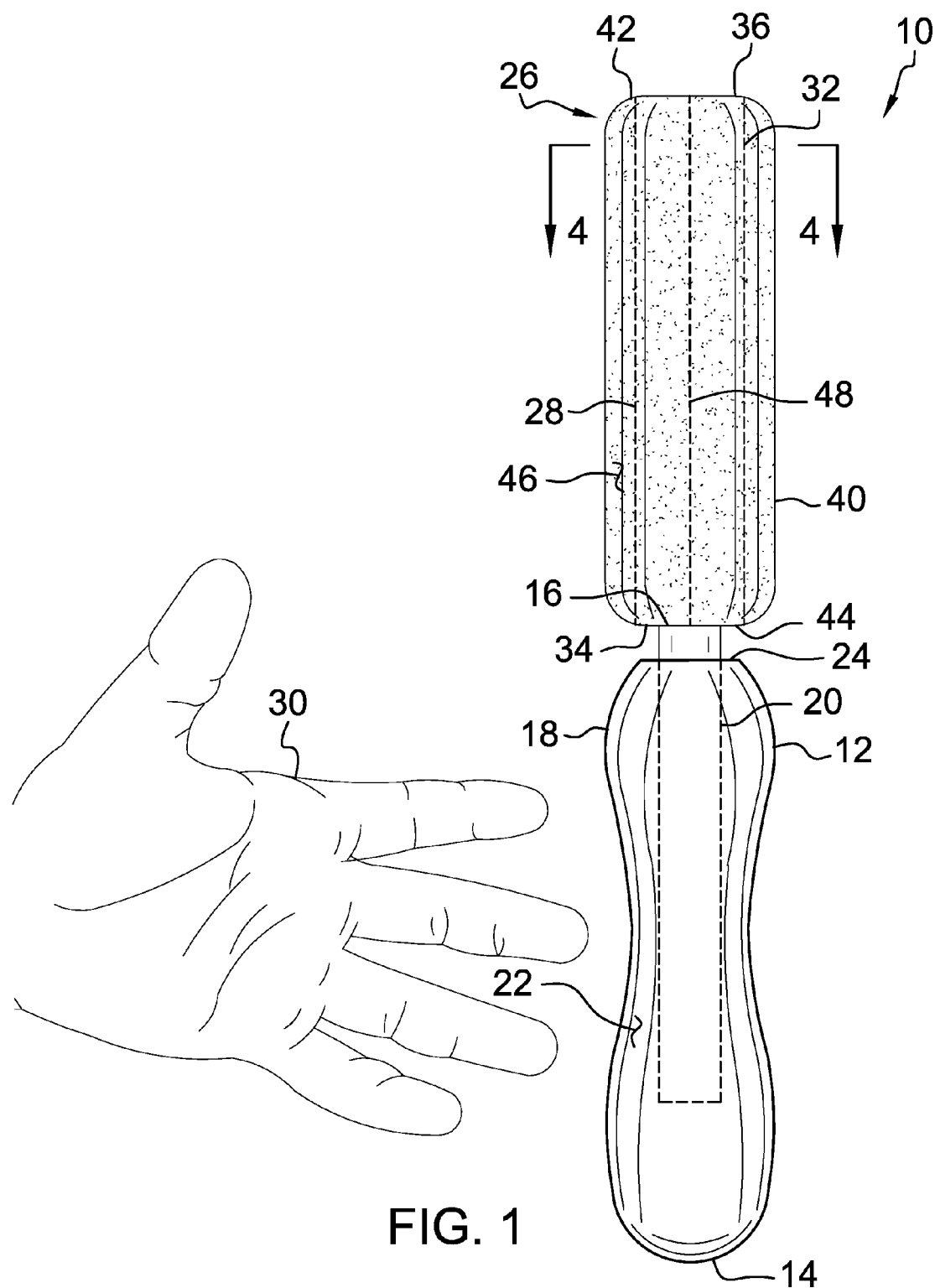
FIG. 1 is a right side view of a cream application assembly according to an embodiment of the disclosure.
Figure 2:
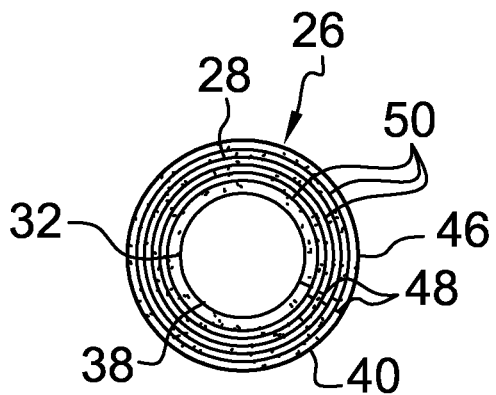
FIG. 2 is a top view of an embodiment of the disclosure.
Figure 3:
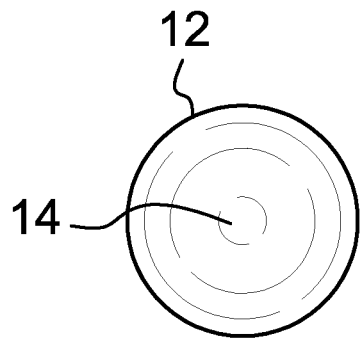
FIG. 3 is a bottom view of an embodiment of the disclosure.
Figure 4:
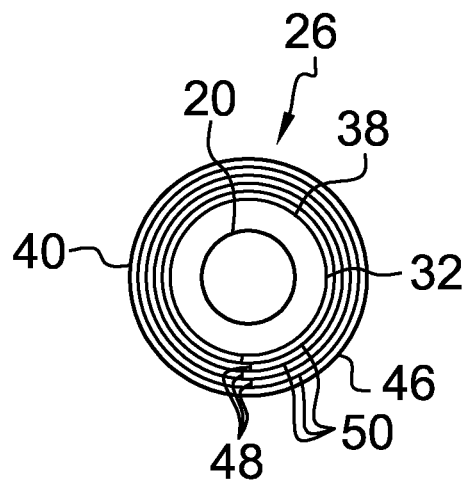
FIG. 4 is a cross sectional view taken along line 4-4 of FIG. 1 of an embodiment of the disclosure.

With reference now to the drawings, and in particular to FIGS. 1 through 6 thereof, a new application device embodying the principles and concepts of an embodiment of the disclosure and generally designated by the reference numeral 10 will be described.

As best illustrated in FIGS. 1 through 6, the cream application assembly 10 generally comprises a handle 12 that has a first end 14 and a second end 16. The handle 12 has a first portion 18 slidably coupled to a second portion 20 such that the handle 12 has a telescopically adjustable length. The first portion 18 of the handle 12 has an outermost surface 22 and the outermost surface 22 curves inwardly between the first end 14 of the handle 12 and an upper threshold 24 of the first portion 18. The first portion 18 of the handle 12 may be gripped and the second portion 20 of the handle 12 may have a diameter that is less than a diameter of the first portion 18. Additionally, the telescopically adjustable length of the handle 12 may range between approximately 6 inches and 12 inches.

An applicator 26 is provided that is rotatably coupled to the handle 12 and the applicator 26 is infused with a cream 28. The cream 28 may comprise a skin lotion, a sun screen or other cosmetically utilized, viscous cream and the applicator 26 applies the cream 28 to a user 30. The applicator 26 comprises a roller 32 that has a first end 34, a second end 36 and an outer surface 38 extending between the first end 34 and the second end 36. The first end 34 of the roller 32 is rotatably coupled to the second end 16 of the handle 12 and the roller 32 is elongated between the first end 34 of the roller 32 and the second end 36 of the roller 32. The outer surface 38 is arcuate such that the roller 32 has a cylindrical shape. The roller 32 may be comprised of a resiliently compressible material.

A strip 40 is provided that has a top edge 42, a bottom edge 44 and an outward surface 46 extending between the top edge 42 and the bottom edge 44. The strip 40 is wrapped around the roller 32 such that the bottom edge 44 is positioned adjacent to the first end 34 of the roller 32 and the top edge 42 is positioned adjacent to the second end 36 of the roller 32. The strip 40 is infused with the cream 28 and the outward surface 46 may be positioned against the user 30. The outward surface 46 selectively releases the cream 28 when the outward surface 46 is positioned against the user 30 thereby facilitating the strip 40 to apply and distribute the cream 28 on the user 30.

The strip 40 has a plurality of perforations 48 extending between the top edge 42 and the bottom edge 44 and the perforations 48 are spaced apart from each other and distributed along the strip 40 to define a plurality of sheets 50. The perforations 48 are sufficiently spaced apart from each other such that each of the sheets 50 fully extends around an entire circumference of the roller 32. Each of the sheets 50 is removable from the strip 40 when the sheet 50 becomes depleted of the cream 28.

Figure 5:
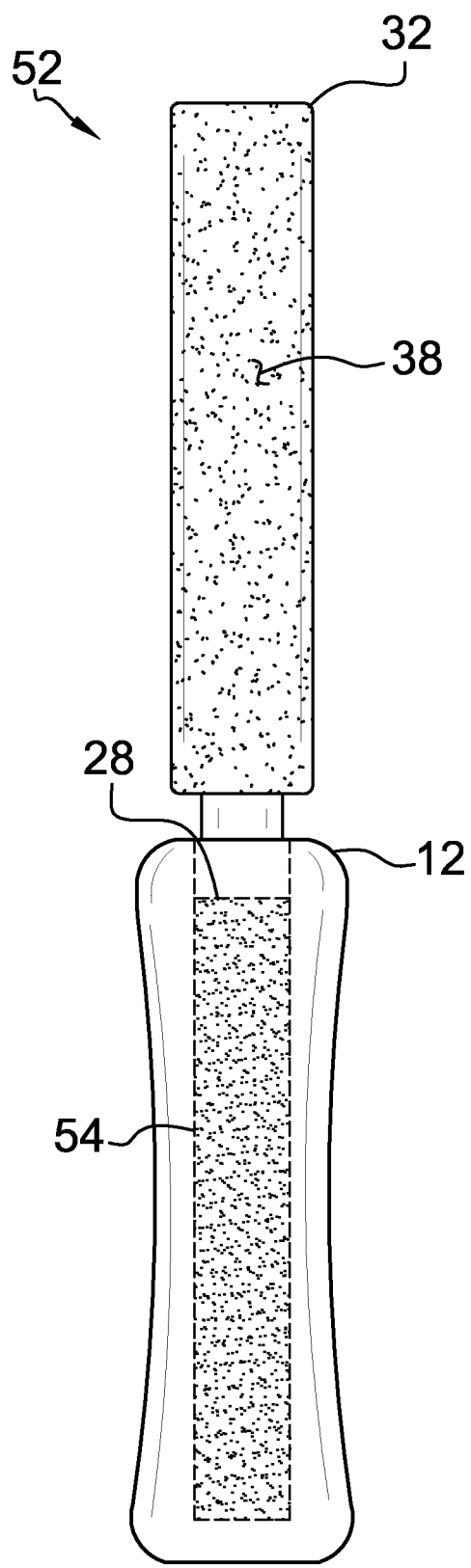
FIG. 5 is a perspective view of an alternative embodiment of the disclosure.
Figure 6:
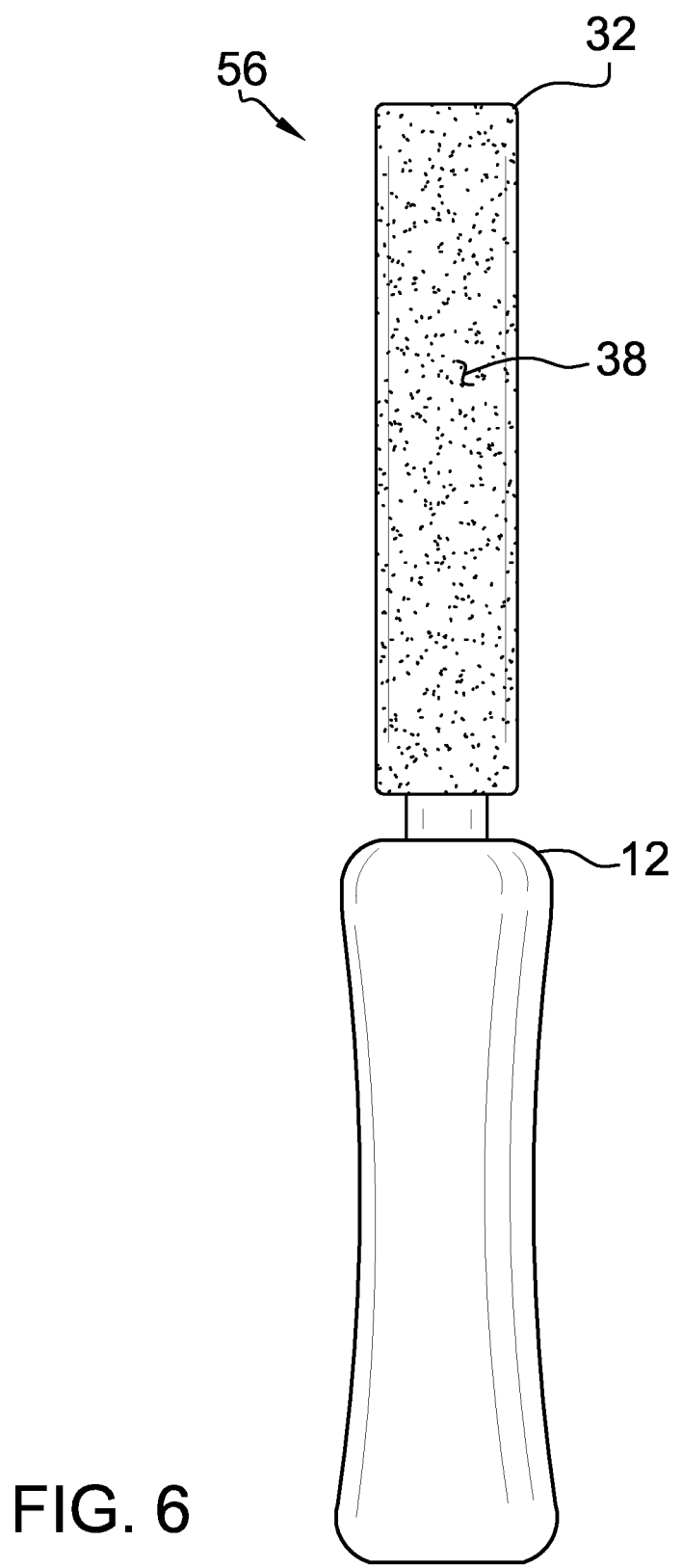
FIG. 6 is a right side view of an alternative embodiment of the disclosure.

In an alternative embodiment 52 as shown in FIG. 5, the handle 12 may be substantially hollow to define a cream reservoir 54 within the handle 12 and the cream reservoir 54 may be filled with the cream 28. The roller 32 may be in fluid communication with the cream reservoir 52 thereby facilitating the outer surface 38 of the roller 32 to be infused to the cream 28 such that the cream 28 may be applied to and distributed on the user 30. In an alternative embodiment 56 as shown in FIG. 6, the handle 12 may be solid between the first end 14 and the second end 16. The cream 28 may be manually applied to the user 30 and the roller 32 may be used to distribute the cream 28 on the user 30.

In use, the outward surface 46 of the strip 40 is rolled against the user 30 and the cream 28 is applied to and distributed on the user 30. The exposed sheet 50 is removed from the strip 40 once the exposed sheet 50 becomes depleted of the cream 28, thusly exposing a fresh sheet 50 that is fully infused with the cream 28. A desired number of sheets 50 is utilized and discarded while the cream 28 is applied to the user 30. The length of the handle 12 is adjusted thereby facilitating the cream 28 to be applied on areas of the user 30 that are difficult to reach.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A cream application assembly configured to apply a cream to a user, said assembly comprising:

a handle having a first end and a second end, said handle having a first portion slidably coupled to a second portion such that said handle has a telescopically adjustable length; and an applicator rotatably coupled to said handle, said applicator being infused with a cream, said applicator being configured to apply the cream to a user, said applicator comprising:

a roller having a first end, a second end and an outer surface extending between said first end and said second end, said first end of said roller being rotatably coupled to said second end of said handle, said roller being elongated between said first end of said roller and said second end of said roller, said outer surface being arcuate such that said roller has a cylindrical shape; and a strip having a top edge, a bottom edge and an outward surface extending between said top edge and said bottom edge, said strip being wrapped around said roller such that said bottom edge is positioned adjacent to said first end of said roller and said top edge is positioned adjacent to said second end of said roller, said strip being infused with the cream, said outward surface being configured to be positioned against the user, said outward surface being configured to selectively release the cream when said outward surface is positioned against the user thereby facilitating said strip to distribute the cream on the user, said strip having a plurality of perforations extending between said top edge and said bottom edge, said perforations being spaced apart from each other and distributed along said strip to define a plurality of sheets, said perforations being sufficiently spaced apart from each other such that each of said sheets fully extends around an entire circumference of said roller, each of said sheets being configured to be removable from said strip when said sheet becomes depleted of the cream.

* * * * *